United States Patent [19]

Gaffney et al.

[11] Patent Number: 4,795,842
[45] Date of Patent: Jan. 3, 1989

[54] METHANE CONVERSION PROCESS

[75] Inventors: Anne M. Gaffney, West Chester; C. Andrew Jones, Newtown Square; John A. Sofranko, West Chester, all of Pa.

[73] Assignee: Atlantic Richfield Company, Los Angeles, Calif.

[21] Appl. No.: 81,400

[22] Filed: Aug. 4, 1987

[51] Int. Cl.⁴ ............................................. C07C 2/00
[52] U.S. Cl. .................................. 585/400; 585/415; 585/417; 585/500; 585/516; 585/654; 585/700; 585/832; 585/943
[58] Field of Search ............... 585/415, 500, 400, 417, 585/541, 700, 943, 418, 654, 656, 658, 661

[56] References Cited

U.S. PATENT DOCUMENTS

| | | | |
|---|---|---|---|
| 4,450,310 | 5/1984 | Fox et al. | 585/400 |
| 4,507,517 | 3/1985 | Devries et al. | 585/415 |
| 4,513,164 | 4/1985 | Olah | 585/700 |
| 4,544,785 | 10/1985 | Withers et al. | 585/500 |
| 4,547,608 | 10/1985 | Johnson | 585/500 |
| 4,547,611 | 10/1985 | Jones et al. | 585/500 |
| 4,560,823 | 12/1985 | Gaffney | 585/654 |
| 4,568,785 | 2/1986 | Jaecker | 585/500 |
| 4,593,139 | 6/1986 | Withers | 585/500 |
| 4,620,057 | 10/1986 | Kimble et al. | 585/500 |

*Primary Examiner*—Asok Pal
*Attorney, Agent, or Firm*—William C. Long

[57] ABSTRACT

The invention relates to the conversion of methane to higher hydrocarbons by contact with a solid oxidative synthesizing agent, the specific improvement being the addition to the reaction system of one or more components of the oxidative synthesizing agent which are lost during the reaction.

9 Claims, No Drawings

METHANE CONVERSION PROCESS

BACKGROUND OF THE INVENTION

This invention relates to the conversion of methane to higher hydrocarbons. A particular application of this invention is a method for converting natural gas to more readily transportable material.

Methane can be converted to higher hydrocarbons by reaction at conditions of elevated temperature - e.g. a temperature selected within the range from about 500° C. to about 10000° C. For example, methane can be contacted with an oxidative synthesizing agent at such elevated temperatures in order to produce higher hydrocarbons. Oxidative synthesizing agents are compositions having as a principal component at least one oxide of at least one metal which compositions produce $C_2+$ hydrocarbon products, co-product water, and a composition comprising a reduced metal oxide when contacted with methane at synthesizing conditions. Reducible oxides of several metals have been identified which are capable of converting methane to higher hydrocarbons. In particular, oxides of manganese, tin, indium, germanium, lead, antimony, bismuth, praseodymium, terbium, cerium, iron and ruthernium are most useful. See commonly-assigned U.S. Pat. Nos. 4,443,644 (Sb); 4,443,649 (Mn); 4,444,984 (Sn); 4,445,648 (In); 4,443,645 (Ge); 4,443,674 (Pb); 4,443,646 (Bi); 4,499,323 (Pr); 4,499,324 (Ce); and 4,593,139 (Ru), the entire contents of which are incorporated herein by reference. See also commonly-assigned U.S. patent application Ser. No. 06/666,694 (Fe) the entire content of which is incorporated herein by reference.

Commonly-assigned U.S. Pat. No. 4,554,395 discloses and claims a process which comprises contacting methane with an oxidative synthesizing agent under elevated pressure (2-100 atmospheres) to produce greater amounts of $C_2+$ hydrocarbon products.

Commonly-assigned U.S. Pat. No. 4,560,821 discloses and claims a process for the conversion of methane to higher hydrocarbons which comprises contacting methane with particles comprising an oxidative synthesizing agent which particles recirculate between two physically separate zones—a methane contact zone and an oxygen contact zone.

U.S. Pat. No. 4,499,322 discloses and claims a process for the conversion of methane to higher hydrocarbon and comprises contacting methane with a oxidative synthesizing agent containing a promoting amount of alkali metal and/or compounds thereof.

U.S. Pat. No. 4,495,374 discloses and claims a process for the conversion of methane to higher hydrocarbons which comprises contacting methane with an oxidative synthesizing agent containing a promoting amount of alkaline earth metal and/or compounds thereof.

Hinsen and Baerns report studies of a continuous mode for the oxidative coupling of methane wherein regeneration air is cofed with methane feed. Hinsen, W. and Baerns, M., "Oxidative Koppling von Methan zu $C_2$- Kohlenwasserstoffen in Gegenwart unterschiedlicher Katalsatoren", Chemiker-Zeitung, Vol. 107, No. 718, pp. 223-226 (1983). Using a catalyst based on lead oxide and gamma-alumina in a fixed bed reactor operated at 1 atmosphere total pressure and 600-750 degrees C. they report results of approximately 53% selectivity to ethane and ethylene at 8% methane conversion for a feed consisting of about 50% methane, 25% air and 25% nitrogen. Other metal oxides studied by Hinsen and Baerns included oxides of Bi, Sb, Sn and Mn.

U.S. Pat. No. 4,523,049, discloses and claims a process for converting methane to higher hydrocarbons which comprises contacting methane and an oxygen-containing gas with a solid comprising a reducible metal oxide and an alkali/alkaline earth metal promotor.

U.S. Pat. No. 4,523,050 discloses and claims a process for converting methane to higher hydrocarbons which comprises contacting methane and an oxygen-containing gas with a manganese silicate.

Commonly-assigned U.S. patent application Ser. No. 06/738,110, filed May 24, 1985, discloses and claims a method for converting methane to higher hydrocarbons wherein methane and a gaseous oxidant are contacted with a nonacidic solid. In a preferred embodiment, the solid comprises an alkali metal component associated with a support material. The application also teaches conducting the contacting in the presence of halogen promotors when employing alkali-promoted solids.

Commonly-assigned U.S. patent application Ser. No. 6/738,114, filed May 24, 1985, discloses and claims a process wherein methane and a gaseous oxidant are contacted with a nonacidic solid in the presence of halogen promotor but in the absence of an alkali metal promotor.

Commonly-assigned U.S. patent application Ser. No. 014,406 discloses and claims a method for converting methane to higher hydrocarbons wherein methane and added water are contacted in the substantial absence of added gaseous oxidant with a solid comprising at least one reducible metal oxide.

Commonly-assigned U.S. patent application Ser. No. 014,405 discloses and claims a method for converting methane to higher hydrocarbons wherein methane and a gaseous oxidant together with added water are contacted with a nonacidic solid and/or a reducible metal oxide.

The reaction products of the foregoing processes are hydrocarbons, carbon oxides, coke and water.

A problem in the past has been a decline in the activity of the solid contact materials, especially where alkali metals such as lithium form a component of the contact solid. Upon prolonged use at the reaction conditions necessary for methane conversion, activity of the contact solids tends to decline as manifested by lowered methane conversion until the activity becomes uneconomically low. Selectivity also declines.

SUMMARY OF THE INVENTION

It has now been found that the decline in activity and selectivity of the solid contact material is caused to a considerable extent by loss of important components from the contact solid at the conditions of methane conversion, and that problems of activity and selectivity decline can be substantially overcome by adding to the reaction system either continuously or intermittently those components which tend to be lost from the contact solid.

DETAILED DESCRIPTION OF THE INVENTION

The present invention is applicable to processes of the "redox" type where methane is contacted with a reducible metal oxide in the substantial absence of gaseous oxidant and the reduced metal oxide is regenerated in a separate oxidizing step, as well as to processes of the "cofeed" type where gaseous oxidant is incorporated with methane in the gaseous feed to the reaction system. In an especially preferred practice, a promoting amount of halide material is added to the reaction system in conjunction with the addition of the contact solid component.

In one embodiment of the invention, methane is converted to higher hydrocarbons by contact at reactive conditions with a reducible metal oxide oxidative synthesizing agent. This contact can be carried out in the "redox" mode wherein methane is contacted with the reducible oxide in the absence of added gaseous oxidant and subsequently the reduced oxide is oxidized by contact with oxidant gas in the substantial absence of methane. See, for example, U.S. Pat. Nos. 4,443,649, 4,444,984, 4,445,648, 4,443,645, 4,443,674, 4,443,646, 4,499,323, 4,499,324 and 4,593,139 for an extensive description of this mode of operation.

Alternatively, the invention can be practiced by contacting a mixture of methane and gaseous oxidant at reactive conditions with an appropriate contact solid in the "cofeed" mode of the invention. In this case, as further described below, the contact solid may comprise a reducible metal oxide oxidative synthesizing agent component or it may comprise a nonacidic solid with or without the additional presence of reducible metal oxide.

The essential feature of the invention provides for the addition to the reaction system of one or more components of the contact solid without substantial interruption of the reaction.

An especially advantageous practice involves conversion systems wherein an alkali metal containing contact material is employed, with or without a reducible metal oxide as an additional component of the contact solid. Such contact solids are particularly illustrated in US Pat. No. 4,499,322, U.S. Pat. No. 4,523,049, commonly assigned U.S. patent application Ser. No. 06/738,110 filed May 24, 1985, and the like.

In accordance with the invention, while the reaction system is essentially at reaction conditions, one or more components of the contact solid are added to the system in order to maintain the system reactivity. Systems employing an alkali metal component as part of the contact solid are especially advantageously treated by the procedure of the invention. The alkali metal, preferably as a compound thereof, and most preferably as a halide, is fed to the reaction system either continuously or intermittently at a rate which is effective to prevent excessive decline in activity of the system.

In a cofeed operation, the added compound, e.g. an alkali metal halide, can be introduced in powdered form or as a solution, for example, in water, with the gaseous methane/oxidant feed continuously or on an intermittent basis at the rate necessary to sustain high system activity. Alternatively, the methane and/or oxidant feed can be temporarily interrupted while the component is added but this is not preferred.

In a redox system the component can be added either with the methane during the methane conversion portion of the cycle or with the oxidant during the oxidation of the reducible metal oxide part of the cycle or during both parts of the cycle; addition during the oxidation is preferred.

The appropriate amount of the solid contact material component is that which is necessary to maintain appropriate selectivity and activity of the system and can readily be determined either by trial and error or by monitoring the rate at which contact solid components are lost from the system and adding such components at the same or a higher rate.

With regard to reducible metal oxides, while such solids are sometimes referred to as "catalysts" it will be understood that, under conditions of use, nonacidic solids comprising a reducible metal oxide act as selective oxidants, and, therefore, take on the characteristics of a reactant during use. Thus, for example, the term "Mn-containing oxides" is meant to embrace both reducible oxides of Mn and reduced oxides of Mn, it being understood reducible oxides comprise the principal active component of the compositions.

In their active state, such catalysts comprise at least one reducible oxide of at least one metal, which oxide when contacted with methane at synthesizing conditions (e.g. at a temperature within the range of about 500° to 10000° C.) produces higher hydrocarbon products, coproduct water, and a reduced metal oxide. The term "reducible" is used to identify those oxides of metals which are reduced under the aforesaid conditions. The term "reducible oxides of metals" includes: (1) compounds described by the general formula $M_xO_y$ wherein M is a metal and x and y designate the relative atomic proportions of metal and oxygen in the composition and/or (2) one or more oxygen-containing metal compounds (i.e., compounds containing elements in addition to the metal O), provided that such oxides and compounds have the capability of producing higher hydrocarbon products from methane as described herein.

Effective agents for the conversion of methane to higher hydrocarbons have previously been found to comprise reducible oxides of metals selected from the group consisting of manganese, tin, indium, germanium, antimony, lead, bismuth and mixtures thereof. See U.S. Pat. Nos. 4,443,649; 4,444,984; 4,443,648; 4,443,645; 4,443,647; 4,443,644; and 4,443,646. Reducible oxides of manganese are particularly preferred catalyst components.

Reducible oxides of cerium, praseodymium, and terbium have also been found to be effective for the conversion of methane to higher hyrrocarbons, particularly associated with an alkali metal component and/or an alkaline earth metal component. See U.S. Pat. Nos. 4,499,324 (Ce) and 4,499,323 (Pr) and also see commonly-assigned U.S. patent application Ser. No. 06/600,918 (Tb).

Reducible oxides of iron and ruthenium are also effective, particularly when assoicated with an alkali or alkaline earth oomponent. See commonly-assigned U.S. patent application No. 06/600,730 (Fe) and U.S. Pat. Nos. 4,489,215 and 4,593,139 (Ru).

Alkali and alkaline earth metals and compounds thereof have been found to improve the hydrocarbon product selectivity of reducible metal oxides. The further incorporation of phosphorous into solids promoted by alkali or alkaline earth components enhances catalyst stability. See commonly-assigned U.S. Pat. Nos. 4,499,322 and 4,495,374, the entire content of which are incorporated herein by reference. Alkali metals are selected from the group consisting of lithium, sodium, potassium, rubidium and cesium. Lithium, sodium and potassium, and especially lithium and sodium, are preferred alkali metals. Alkaline earth metals are selected from the group consisting of magnesium, calcium, strontium and barium. Presently preferred members of this group are magnesium and calcium. Compositions derived from magnesia have been found to be particularly effective catalyst materials. Boron and compounds thereof are also desirably present in the reducible metal oxide catalyst employed in the process of this invention. See commonly-assigned U.S. patent application Ser. No. 06/877,574, the entire content of which is incorporated herein by reference. One class of boron-promoted compositions useful in the process of this invention comprises:

(1) at least one reducible metal oxide,
(2) at least one member of the group consisting of boron and compounds thereof, and
(3) at least one member of the group consisting of oxides of alkaline earth metals.

A related class of catalyst compositions further comprises at least one alkali metal or compound thereof. Sodium and lithium are preferred alkali metal components.

One further, special class of catalyst compositions useful in the process of this invention are mixed oxides of sodium, magnesium, manganese and boron characterized by the presence of the crystalline compound $NaB_2Mg_4Mn_2O_x$ wherein x is the number of oxygen atoms required by the valence states of the other elements, said compound having a distinguishing x-ray diffraction pattern. In its most active form, the compound is believed to correspond to the formula $NaB_2Mg_4Mn_2O_{11}$. While this crystalline compound has been found to be associated with highly effective oxidant compositions, it has further ben found that still better results are obtained when the oxidant is characterized by both: (1) the presence of crystalline compound $NaB_2Mg_4Mn_2O_x$ and (2) a stoichiometric excess of Mn relative to at least one of the other elements of the crystalline compound. In currently preferred oxidants of this type, a stoichiometric excess of Mn relative to B is provided. In a still more specific preferred embodiment excess amounts of Na and Mg, as well as Mn, are present in the mixed oxide composition relative to the amounts required by the amount of boron present to satisfy the stoichiometry of the compound $NaB_2Mg_4Mn_2O_x$.

Further examples of components which may be present in the catalysts used in the process of this invention are halogen and chalcogen components. Such components may be added either during preparation of the catalysts or during use. Methane conversion processes employing halogen-promoted reducible metal oxides are disclosed in U.S. Pat. No. 4,544,784. Methane conversion processes employing chalcogen-promoted, reducible metal oxides are disclosed in U.S. Pat. No. 4,544,785.

The reducible metal oxides compositions may be supported by or diluted with support materials such as silica, alumina, titania, zirconia and the like, and combinations thereof. When supports are employed, alkaline earth oxides, especially magnesia, are preferred.

The catalysts are conveniently prepared by any of the methods associated with similar compositions known in the art. Thus, such methods as precipitation, co-precipitation, impregnating, granulation, spray drying or dry-mixing can be used. Supported solids may be prepared by methods such as adsorption, impregnation, precipitation, co-precipitation, and dry-mixing. For example, compounds of Mn,Sn,In,Ge,Pb,Sb,Bi,Pr,Tb,Ce,Fe and/or Ru may be combined with compounds of other components in any suitable way. Substantially any compound of the components can be employed. Compounds typically used would be oxides or organic or inorganic salts of the recited components.

To illustrate, when preparing a catalyst containing: (1) a reducible metal oxide component (e.g., Mn), (2) an alkali metal component, (3) a boron component and (4) an alkaline earth component; one suitable method of preparation is to impregnate compounds of the fourth component of the composition with solutions of compounds of Mn, alkali metals, and/or boron. Suitable compounds for impregnation include the acetates, acetyl acetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solid is calcined at a temperature selected within the range of about 300° to 1200° C. Particular calcination temperatures will vary depending on the compounds employed. Preferably, the alkaline earth component is provided as the oxide. Preferably, th alkali metal component is provided as a basic composition of the alkali metal(s). Examples are sodium hydroxide, sodium acetate, lithium hydroxide, lithium acetate, etc. When P is employed as an additive, it has been found desirable to add the alkali metal and P to the composition as compounds such as the orthophosphates, metaphosphates, and pyrophosphates of alkali metals. Pyrophosphates are preferred. Sodium pyrophosphate is particularly preferred. Preferably, the boron component is provided as boric acid, boric oxide (or anhydride), alkali metal borates, boranes, borohydrides, etc., especially boric acid or oxide.

Formation of the crystalline compound $NaB_2Mg_4Mn_2O_x$ may be accomplished by reacting active compounds of the substituent elements. A suitable mixture of the reactive compounds is formed and heated for a time sufficient to form the crystalline material. Typically, a temperature of about 850° to about 950° C. is sufficient. When preparing mixed oxide compositions characterized by the presence of other crystalline compounds, the composition is desirably incorporated with binders or matrix materials such as silica, alumina, titania, zirconia, magnesia and the like.

Regardless of which particular catalyst is prepared or how the components are combined, the resulting composite will generally be dried and calcined at elevated temperatures prior to use. Calcination can be done under air, $H_2$, carbon oxides, steam, and/or inert gases such as $N_2$ and the noble gases.

Preferably, methane is contacted with reducible metal oxides in the presence of added water and in the substantial absence of catlytically effective nickel, noble metals and compounds thereof, (i.e., nickel, rhodium, palladium, silver, osmium, iridium, platinum and gold) to minimize the deleterious catalytic effects thereof. These metals, when contacted with methane at the temperatures employed in the methane contacting step of the present invention, tend to promote coke formation, and the metal oxides tend to promote the formation of combustion products rather than the desired hydrocarbons. The term "catalytically effective" is used herein to identify the quantity of one or more of nickel and the noble metals and compounds thereof which substantially changes the distribution of products obtained in the method of this invention relative to such contacting in the absence of such metals and compounds thereof.

Regardless of which class of contacting solid is selected (i.e., reducible or nonreducible solid), operating temperatures are generally within the range of about 300° to about 1200° C.

If nonacidic solids are employed without the presence of reducible metal oxides, operating temperatures are preferably within the range of about 700° to about 1200° C., more preferably about 800° to about 1000° C.

If reducible metal oxides are employed, the temperature selected may depend in part on the particular reducible metal oxide(s) employed. Best results for contact solids containing manganese have been found at operating temperatures within the range of about 800° to 900° C.

The solids useful in the present invention are characterized as "nonacidic". This description is meant to refer to the main, predominant surface properties of the nonacidic solids. For example, some solid bases are known to have acidic properties to some extent. See Tanabe, K., "Solid Acid and Base Catalysts." *In: Catalysis Science & Technology*, Vol. 2 (New York, Springer-Verlag Berlin Heidelberg, 1981). Currently preferred nonacidic solids used in the present process are characterized by negligible acidity (less than about 0.01 meg/gm) in the $H_o$ range less than about 3.3, preferably less than about 6.8. Ho is the Hammett acidity parameter described on pp. 234–241 of Tanabe.

A further characteristic of preferred nonacidic solids for the present process is a relatively low surface area;. Nonacidic solids having surface areas less than about 50 $m^2/gm$ are suitable, but the surface areas of preferred solids are within the range of about 0.01–10 $m^2/gm$.

In one distinct embodiment of this invention, methane and a gaseous oxidant are contacted with a non-acidic solid characterized by the substantial absence of reducible metal oxides. Characteristics of nonacidic solids preferred for this embodiment are that they be stable and substantially nonreducible under process conditions. Examples of suitable nonacidic solids include those solid bases described in Table 2 on p. 233 of Tanabe, supra. However, presently preferred nonacidic solids are metal oxides and mixed oxides. Alkaline earth oxides are particularly preferred, especially MgO and CaO. Other suitable metal oxides are $SiO_2$, alpha-$Al_2O_3$, $La_2O_3$, $ThO_2$, $TiO_2$, $TiO_2$, and $ZrO_2$. Such materials are relatively stable under the conditions of the present process.

Alkali metal-promoted alkaline earth oxides are preferred nonacidic solids for this embodiment. Such solids are described and exemplified in commonly-assigned U.S. patent application Ser. No. 06/738,110, filed May 24, 1985, the entire content of which is incorporated herein by reference. Halogen promoters may be employed.

The methane containing hydrocarbon feedstock employed in the process of this invention may contain in addition to methane other hydrocarbon or non-hydrocarbon components. The methane content of the hydrocarbon portion of the feedstock, however, will typically be within the range of about 40 to 100 vol. %, preferably within the range of about 80 to 100 vol. %, more preferably within the range of about 90 to 100 vol. %.

Where gaseous oxidant is cofed, the oxidant preferably comprises a gas containing molecular oxygen (e.g., air). However, oxides of nitrogen, esp. $N_2O$, have also been found to be effective gaseous oxidants. See U.S. Pat. No. 4,547,610, the entire content of which is incorporated herein by reference.

The ratio of hydrocarbon feedstock to oxygen-containing gas is not narrowly critical to the present invention. Generally, it is desirable to control the hydrocarbon/oxygen molar ratio to avoid the formation of gaseous mixtures within the flammable region. Preferably, the ratio is maintained within the range of about 0.1–300:1, more preferably within the range of about 1–150:1. Methane/air feed mixtures containing about 30 to 90 volume % methane have been found to comprise a desirable feedstream. Further dilution of the feedstream with gases such as nitrogen may be beneficial for improved temperature control.

The provision of added water during at least a portion of the methane/solid contacting is advantageous as described in copending applications Ser. Nos. 07/014,405 and 07/014,406, each filed Feb. 13, 1987. Preferably, the mole ratio of added water to methane in the gas to be contacted is less than about 10. More preferably, this mole ratio is in the range of about 0.01 to about 6, still more preferably about 0.05 to about 4.0. The added water may be combined with the methane-containing gas and/or the oxygen-containing gas prior to contacting the nonacidic solid. For example, the methane-containing gas or the oxygen-containing gas may be contacted with water so that the gas "picks-up" a predetermined, controlled amount of added water prior to the methane/solid contacting. Alternately, a predetermined, controlled amount of water e.g., steam, can be injected into the methane-containing gas and/or the oxygen-containing gas and/or directly into the methane/solid contacting zone or zones.

Operating pressures are not critical to the presently claimed invention. However, both general system pressure and partial pressures of methane and water have been found to effect overall results. Preferred general system pressures are within the range of about 0.1 to 30 atmospheres.

The space velocity of the gaseous reaction streams are similarly not critical to the presently claimed invention, but have been found to effect overall results. Preferred total gas hourly space velocities are within the range of about 100 to 300,000 hr.$^{-1}$, more preferably within the range of about 600 to 100,000 hr.$^{-1}$.

Contacting methane and a reducible metal oxide to form higher hydrocarbons from methane also produces coproduct water and reduces the metal oxide. The exact nature of the reduced metal oxides are unknown, and so are referred to as "reduced metal oxides". Regeneration of reducible metal oxides in the method of the present invention occurs "in situ"—by contact of the reduced metal oxide with the oxygen cofed with methane to the contact zone, or during the oxidizing gas contact part of the redox cycle.

The solids may be maintained in the contact zone as fixed, moving, or fluidized beds of solids.

The effluent from the contact zones contains higher hydrocarbon products (e.g., ethylene, ethane and other light hydrocarbons), carbon oxides, water and unreacted hydrocarbons (e.g., methane). Higher hydrocarbons may be recovered from the effluent and, if desired, subjected to further processing using techniques known to those skilled in the art. Unreacted methane may be recovered and recycled to the contact zone.

The essential feature of the present invention resides in the addition to the reaction system of components of the solid contact agent which are lost from the solid contact agent at the severe conditions necessary for the methane conversion.

As pointed out above, the alkali metals are advantageously incorporated in the contact solids which are used for methane conversion. It has been found that at the synthesis temperatures necessary for methane conversion these alkali metals are gradually lost from the contact solids with the result that the contact solids significantly decline in selectivity and activity upon prolonged use.

The invention is not, however, limited just to addition of alkali metals to the reaction system. Alkaline earth metal components, reducible metal oxide components, boron, phosphorous components and the like may also be lost from the contact solid upon use.

It is a feature of this invention that decline in the activity of the contact solid is substantially lessened by addition to the reaction zone at the synthesis conditions of those components of the contact solid which the solid tends to be depleted in.

In especially preferred practice the alkali metals, most notably lithium and sodium are added. Reducible metal oxides such as those of manganese are appropriately added as are boron and phosphorous materials.

The solid contact components can be added in the form of compounds thereof such as acetates, acetyl acetonates, oxides, carbides, carbonates, hydroxides, formates, oxalates, nitrates, phosphates, sulfates, sulfides, tartrates, fluorides, chlorides, bromides, iodides, and the like.

Especially outstanding results are achieved where halide, expecially chloride, is added in conjunction with the addition of the contact solid component. For example, the oontact solid can be added as the halide. Alternatively, halide and the contact solid component can be added as separate materials—e.g. coaddition of LiOH and $Cl_2$ or HCl or the like.

Addition of the contact solid component, preferably in conjunction with halide can take place during the methane conversion thus avoiding the necessity of shutting down the reaction system or interrupting the reaction. The amount of contact solid component added corresponds closely to the amount lost from the contact material—no special advantages result from addition of larger amounts. Most suitably, the added materials are incorporated as powder or aqueous solution with the gaseous feed to the reaction system. In the cofeed mode the materials are added continuously or intermittently with the methane/oxidant feed. In the redox mode the materials can be added at any part of the cycle but preferably are added with the oxidant during the reducible metal oxide reoxidation portion of the cycle.

The following examples illustrate the invention.

EXAMPLE 1

An oxidative synthesizing agent catalyst was prepared by mixing (in a ball mill) manganese dioxide (33.2 grams), boric acid (11.8 grams), lithium hydroxide (4.6 grams) and magnesium oxide (43.1 grams) corresponding to an atomic ratio of Li/B/Mn/Mg of about 0.5/0.5/1.0/2.8. Silicon dioxide was added in the amount of 6.5 wt % of the final composition as binder. The mixture was calcined at 900° C. for 16 hours in air and then treated with hydrogen at 900° C. for 3 hrs.

The resulting formulation was ground to 80–140 mesh size and 14.8 grams were changed to an alumina tube of 0.75 inch inside diameter surrounded by a tubular furnace. The reactor temperature was raised and methane was passed upwardly through the fluid bed of oxidative synthesizing agent and reacted to form higher hydrocarbons in a cyclic redox mode of operation. Specifically, methane was passed through the oxidative agent for 30 seconds at a methane WHSV of 0.8 hrs.-1 followed by a nitrogen purge and then reoxidation with air before the cycle was repeated. From time to time additives as indicated in the following table were introduced in powder form with the air during the reoxidation portion of the redox cycle. The reactor effluent was analyzed by gas chromatography. The following Table 1 shows the results obtained. Each group represents the results for consecutive cycles.

TABLE 1

| Reaction Temp, °C. | Additive | $CH_4$ Conversion % | $C_{2+}$ Selectivity % |
|---|---|---|---|
| 725 | none | 4 | 97 |
| 725 | none | 5 | 97 |
| 725 | 0.015 g LiCl | 26 | 92 |
| 725 | none | 24 | 91 |
| 725 | none | 17 | 93 |
| 775 | none | 15 | 89 |
| 775 | none | 16 | 89 |
| 775 | 0.015 LiCl | 38 | 81 |
| 775 | none | 34 | 81 |
| 775 | none | 27 | 89 |
| 825 | none | 27 | 76 |
| 825 | none | 31 | 69 |
| 825 | 0.015 g LiCl | 57 | 56 |
| 825 | none | 23 | 76 |
| 825 | 0.015 g LiCl | 34 | 74 |
| 825 | none | 21 | 84 |
| 825 | none | 22 | 81 |
| 825 | none | 18 | 86 |
| 825 | 0.015 g LiCl | 37 | 77 |
| 825 | none | 28 | 78 |
| 825 | none | 29 | 84 |
| 825 | 0.015 g LiCl | 42 | 78 |
| 825 | none | 26 | 85 |
| 825 | 0.015 g LiCl | 43 | 75 |
| 825 | none | 33 | 80 |
| 825 | none | 19 | 87 |
| 825 | 0.015 g NaCl | 42 | 77 |
| 825 | none | 38 | 79 |
| 825 | none | 26 | 86 |
| 825 | none | 21 | 69 |
| 825 | 0.015 g $NH_4Cl$ | 30 | 59 |
| 825 | none | 24 | 66 |
| 825 | none | 25 | 82 |
| 825 | 0.015 g $MnCl_2.4H_2O$ | 38 | 78 |
| 825 | none | 35 | 73 |
| 825 | none | 28 | 74 |
| 825 | none | 26 | 69 |
| 825 | 0.015 g $MgCl_2.6H_2O$ | 35 | 75 |
| 825 | none | 30 | 70 |

The system was then changed to a cofeed mode by continuously passing a mixture of 50 vol % methane and 50% air upwardly through the catalyst, the methane WHSV being 0.8. Powdered LiCl was added as indicated in the following Table 2. Time in the last column was the time since last additive addition.

TABLE 2

| Reaction Temp, °C. | Additive | $CH_4$ Conversion % | $C_{2+}$ Select. % | Time Min. |
|---|---|---|---|---|
| 750 | none | 3 | 87 | — |
| 750 | 0.015 g LiCl | 21 | 79 | 1 |
| 750 | none | 19 | 84 | 2 |
| 750 | none | 15 | 82 | 10 |
| 750 | none | 8 | 90 | 27 |
| 750 | none | 5 | 88 | 72 |
| 750 | none | 4 | 89 | 102 |
| 750 | 0.045 g LiCl | 28 | 75 | 1 |
| 750 | none | 27 | 82 | 2 |
| 750 | none | 23 | 81 | 10 |
| 750 | none | 10 | 89 | 37 |
| 750 | none | 5 | 88 | 72 |

EXAMPLE 2

An oxidative synthesizing agent catlayst was prepared by mixing (in a ball mill) manganese dioxide (33.2 grams), boric acid (11. grams), lithium hydroxide (4.6 grams) and magnesium oxide (43.1 grams) corresponding to an atomic ratio of Li/B/Mn/Mg of about 0.5/0.5/1.0/2.8. Silicon dioxide was added in the amount of 6.5 wt % of the final composition as binder. The mixture was calcined at 900 for 16 hours in air and then treated with hydrogen at 900° C. for 3 hrs.

The resulting formulation was ground to 14-30 mesh size and 5.23 grams were changed to an alumina reactor tube of 0.5 inch inside diameter surrounded by a tubular furnace. The reactor temperature was raised and methane was passed downwardly through the fixed bed of oxidative synthesizing agent and reacted to form higher hydrocarbons in a cyclic redox mode of operation in an extended life testing program. Specifically, methane was passed through the oxidative agent for 30 seconds at a methane WHSV of 0.75 hrs.-1 followed by a nitrogen purge and then reoxidation with air before the cycle was repeated. Cycle time ranged from 7 to 11 minutes, reaction temperature was 825° C., methane GHSV was 1200 hr.-1, and methane WHSV was 0.75 hr.-1.

After more than 7800 cycles, catalyst performance had declined significantly, especially in selectivity of methane conversion to $C_{2}+$ hydrocarbons. Generally about 19% methane conversion was achieved at about 69% selectivity to $C_{2}+$ hydrocarbons.

Lithium metaborate ($LiBO_2$) was added to the catalyst bed during the oxidation portion of the cycle by introduction of $LiBO_2$ powder with the oxidant gas, the amount added being 1.4 wt % of the catalyst expressed as Li and the life tests were continued. At the 12500 cycle mark performance was 22% methane conversion with 81% selectivity to $C_{2}+$ hydrocarbons.

From these results the significant benefits achieved through practice of the invention are apparent.

We claim:

1. In a process for the conversion of methane to higher hydrocarbons by contact at reactive conditions of gases comprised of methane and molecular oxygen, separately or together, with a bed of particulate solid oxidative synthesizing agent in an oxidative synthesis zone, said solid oxidative synthesizing agent containing at least one component from the group consisting of alkali metal and boron, said component being gradually depleted from said solid oxidative synthesizing agent during said methane conversion, the improvement which comprises separately adding said component to the said reaction zone with said gases at a rate sufficient to substantially maintain the activity of said solid oxidative synthesizing agent, and contacting said solid oxidative synthesis agent in said reaction zone with said separately added component.

2. The process of claim 1 wherein said agent is comprised of an alkali metal component and said alkali metal component is added to the system with said gases.

3. The process of claim 1 wherein said alkali metal is sodium.

4. The process of claim 1 wherein said alkali metal is lithium.

5. the process of claim 1 wherein said agent is comprised of a reducible metal oxide.

6. The process of claim 1 wherein said agent is comprised of manganese.

7. The process of claim 1 wherein said component is added as a halide.

8. The process of claim 1 wherein said component is added in conjunction with a halogen compound.

9. The method of claim 1 wherein the component added is a boron component.

* * * * *